(12) United States Patent
Donnet

(10) Patent No.: US 10,596,076 B2
(45) Date of Patent: Mar. 24, 2020

(54) POWDER MIXTURE, USE OF THE POWDER MIXTURE, AND A POWDER JET DEVICE

(71) Applicant: Ferton Holding S.A., Delemont (CH)

(72) Inventor: Marcel Donnet, St. Jean de Gonville (FR)

(73) Assignee: Ferton Holding S.A., Inc. (CH)

( * ) Notice: Subject to any disclaimer, the term of this patent is extended or adjusted under 35 U.S.C. 154(b) by 176 days.

(21) Appl. No.: 15/022,539

(22) PCT Filed: Sep. 2, 2014

(86) PCT No.: PCT/EP2014/068622
§ 371 (c)(1),
(2) Date: Mar. 16, 2016

(87) PCT Pub. No.: WO2015/032758
PCT Pub. Date: Mar. 12, 2015

(65) Prior Publication Data
US 2016/0220452 A1    Aug. 4, 2016

(30) Foreign Application Priority Data

Sep. 6, 2013   (DE) .................. 10 2013 109 758

(51) Int. Cl.
*A61K 6/033*    (2006.01)
*A61K 6/00*     (2020.01)
*A61Q 11/00*    (2006.01)

(52) U.S. Cl.
CPC ............ *A61K 6/033* (2013.01); *A61K 6/0008* (2013.01); *A61K 6/0067* (2013.01); *A61Q 11/00* (2013.01); *A61K 2800/412* (2013.01); *A61K 2800/87* (2013.01)

(58) Field of Classification Search
CPC .................................................. A61K 6/033
See application file for complete search history.

(56) References Cited

U.S. PATENT DOCUMENTS

| 4,612,053 A | 9/1986 | Brown et al. |
| 6,054,119 A | 4/2000 | Hurme et al. |
| 2006/0280694 A1 | 12/2006 | Peldyak et al. |
| 2009/0175917 A1 | 7/2009 | Engelbrecht et al. |

FOREIGN PATENT DOCUMENTS

| DE | 103 31 583 B3 | 7/2004 |
| DE | 10 2006 046 952 A1 | 4/2008 |
| EP | 0 097 288 B1 | 5/1987 |
| EP | 2 572 699 A1 | 3/2013 |
| WO | WO 97 04741 | 2/1997 |
| WO | WO/2013/041711 | 3/2013 |
| WO | WO2013/041711 † | 3/2013 |
| WO | WO 2013 191903 A1 | 12/2013 |

OTHER PUBLICATIONS

Int. J. Abrasive Technolo, 2009, vol. 2, No. 1, pp. 83-96.
J. Biomed. Mater.Res. P.B, 2011, vol. 98B, No. 2, pp. 210-216.
Ryo Akatsuka, Characteristics of hydroxyapatite film formed on human enamel with the powder jet deposition technique, Journal of Biomedical Materials Research B. Applied Biomaterials, vol. 98B, Issue 2, Aug. 2011, pp. 209-216.†
Miyoko Noji, Characteristics of the hydroxyapatite film deposited on human enamel: deposition of a ceramic film by powder jet deposition technique, Int. J. Abrasive Technology, vol. 2, No. 1, 2009, pp. 83-96.†

† cited by third party

*Primary Examiner* — Benjamin J Packard
(74) *Attorney, Agent, or Firm* — Reed Smith LLP

(57) ABSTRACT

The present invention relates to a powder mixture, in particular for the remineralization of teeth, a powder jet device, in particular for application in the field of dentistry, a use of the powder mixture for producing a means for the remineralization of teeth and to a method for the remineralization of teeth, and a use of a powder mixture in a dental apparatus. The powder mixture comprises a deposition powder which is designed to adhere to tooth surfaces.

9 Claims, No Drawings

POWDER MIXTURE, USE OF THE POWDER MIXTURE, AND A POWDER JET DEVICE

The present invention relates to a powder mixture, in particular for the remineralization of teeth, a powder jet device, in particular for application in the field of dentistry, a use of the powder mixture for producing a means for the remineralization of teeth and to a method for the remineralization of teeth, and a use of a powder mixture in a dental apparatus.

Remineralization is a term used in dentistry meaning the redeposition of destroyed or lost minerals of tooth enamel after prior demineralization. Demineralization is the decalcification by loss of minerals. Thus, remineralization describes the redeposition of minerals into the tooth enamel or the repair of minute enamel lesions. Caries formation in its initial phase can be stopped or healed through remineralization. This can be achieved by the patient taking specific fluoride preparations or such. Also known in prior art are powders which can be depositioned on the teeth to form a remineralization film. However, the prior art means and methods have the disadvantage that the treatment is often unpleasant for patients and also time-consuming. Furthermore, such remineralization films do not adhere to the tooth surface.

It is therefore the object of the present invention to provide a powder mixture, in particular for the remineralization of teeth, a powder jet device, in particular for application in dentistry, a method of remineralizing teeth, and a use of a powder mixture to produce an appropriate remineralization means or to use in a dental device which eliminates the above mentioned disadvantages and is designed such that it forms a stable remineralization film while providing the patient with maximum comfort.

This object is achieved by a powder mixture, by a powder jet device, a method, and appropriate uses as claimed and described below in detailed description.

The teaching of the invention relates to a powder mixture, in particular for the remineralization of teeth, characterized in that the powder mixture comprises a deposition powder designed to adhere to the tooth surfaces. In particular, the powder mixture is designed to form a remineralization film on the tooth surfaces. Advantageously this allows decalcified tooth enamel to be re-enriched and hardened by the deposition of new calcium phosphate. Furthermore, possibly exposed dentinal channels (dentinal tubules) can be closed up again. The dentinal tubules conduct external stimuli such as hot, cold, sweet, sour or contact to the dental nerve. This results in sensitive and hyper-sensitive teeth. According to the hydrodynamic theory described by Brännström (1966), this is caused by the movement of fluid within the dentinal tubules in response to the application of stimuli. Advantageously, the exposed dentinal tubules can be closed up again by the remineralization or demineralization film. The powder mixture is therefore also designed to desensitize the teeth. For the sake of clarity, the term 'remineralization film' will always be used here, which does not exclude that it can also—so to speak—be a desensitizing film.

Expediently, the remineralization film has a thickness between about 100 nm and 2 µm. Such a film, or such a layer, is sufficient to close exposed dentinal tubules and to form a remineralization film on the teeth which advantageously provides inter alia phosphate and calcium for remineralization processes. Such a remineralization film immediately relieves the patients pain. No long-term treatment is necessary. Expediently, it is a powder mixture, i.e. a mixture which comprises at least one component which advantageously is the deposition powder that will be explained in greater detail below. Advantageously, the powder mixture can be applied with a prior art powder jet device used for the cleaning of teeth. Expediently, such powder jet devices include a mixing chamber that can be filled with a powder which is then mixed with a fluid, in particular with water, and with air and applied to, i.e. sprayed on the teeth.

Expediently, the powder mixture is characterized in that it contains a carrier powder which allows it to be applied to the tooth by means of a powder jet. Advantageously, the carrier powder is a cleaning powder, in particular sodium bicarbonate, glycine, alditoles such as erythritol, calcium carbonate or a mixture of these substances. Preferably, the carrier powder—so to speak—serves as a transport means for the deposition powder. In case of a traditional powder jet device, a separate nozzle or mixing arrangement would have to be constructed for the fine deposition powder, since the very small particles of the deposition powder are very difficult to diffuse into the air or to swirl in a mixing chamber or mixing arrangement. This makes application to the tooth surfaces extremely difficult.

Therefore, the powder mixture advantageously includes the carrier powder. Expediently, the deposition powder can adhere to the carrier powder, whereby the carrier powder is—so to speak—used as carrier medium for the deposition powder when the remineralization film is applied. Advantageously, the surface structure of the carrier powder or of the particles of the carrier powder is designed such that the deposition powder can adhere to it. Preferably, this adhesion already takes place in the production or in the mixing of the powder mixture and is maintained while it is kept, for example, in a suitable container or in the mixing chamber of the powder jet device. Preferably, the adhesion is designed such that it is maintained even when the powder mixture is applied to the teeth, i.e. especially during the flight of the powder mixture. Advantageously, the deposition powder adheres to the carrier powder. Also advantageously, the surface structure of the carrier powder is rugged to allow the deposition powder to adhere or to be incorporated. Furthermore, the carrier powder can provide a slipstream function while being applied to the teeth. This can result in the best spray conditions or flight conditions for the disposition powder. Expediently, this is achieved in that the average particle size of the carrier powder is larger than the average particle size (or agglomerate size) of the deposition powder. Thus, advantageously, a powder mixture is provided which can be optimally applied to the tooth surfaces and can remain there for a long time with optimal adhesion.

Advantageously, the carrier powder is also a cleaning powder. Thus, advantageously, the powder mixture provides not only a deposition function but also a cleaning function. Prior cleaning of the tooth surfaces or the teeth in general is particularly advantageous, or under certain circumstances even necessary to fully expose the dentinal tubules before they can be properly closed. It is therefore highly advantageous when the powder mixture provides a deposition function and a cleaning function to allow two different treatment methods, i.e. the cleaning of teeth and the deposition of the powder mixture, with the same (powder jet) device.

The powder mixture according to the present invention is also characterized in that the cleaning powder has a mean particle size between 10 µm and 100 µm, preferably between 15 µm and 50 µm, and even more preferably at about 45 µm. For work in the subgingival region, the mean particle size should not be greater than 45 μm, and preferably not greater than 35 μm, and even more preferably between 10 μm and 30 μm.

Expediently, the powder mixture is characterized in that the powder mixture provides the cleaning function and/or the deposition function, and that the cleaning function and the deposition function can be changed among the volume of fluid with which the powder mixture is mixed. Therefore, advantageously, the powder mixture is designed such that it can be mixed with a fluid, in particular with water. Only then is it possible to achieve the high comfort level while the patient is being treated. Thus, it is certainly known in prior art to apply remineralization films to the teeth by means of a powder. However, these cannot be mixed with water, or if they are mixed with water, they adhere poorly to the tooth surfaces. The water component allows the patient to be comfortable during the treatment, since the mouth would become dry very quickly when a dry powder is applied without water, and this would be very unpleasant for the patient. Furthermore, it results in the formation of dust, which also limits the success of the treatment, since the operator cannot see the teeth and cannot tell which parts have already been treated and which haven't. Advantageously, the powder jet can also be focused with the water jet, since the water expediently encases the powder mixture while it is being diffused into the air. Advantageously, by the volume of the water and its proportion in relation to the powder mixture, it can be switched between the cleaning function and the deposition function. Advantageously, the deposition function and the cleaning function are not provided separately. Both functions are provided jointly by the powder mixture, but the powder mixture can also be adjusted, for example via the mixed water portion, such that either the deposition function or the cleaning function predominates. It is also possible to provide only the cleaning function or only the deposition function. The invention is based on the principle that the cleaning function predominates at higher water volumes and the deposition function predominates at lower water volumes.

Preferably, the powder mixture is characterized in that the deposition mixture is a phosphate powder and that the proportion of the phosphate powder in the powder mixture is preferably about 0.5% to 30%. Especially preferred is a proportion of about 2% to 5%. Advantageously, the powder portions mix readily with the fluid portion. Only that allows the powder mixture to adhere to the teeth and thus to form a remineralization film while providing the greatest possible comfort for the patient.

Also preferably, the powder mixture is characterized in that the deposition powder comprises agglomerates of nano particles and that an agglomerate has a specific surface area of approximately >50 m$^2$/g, preferably >60 m$^2$/g. Weak van der Waals forces are responsible for forming the agglomerates.

Preferably, the powder mixture is characterized in that it has an agglomerate size in the range between about 1 μm and 10 μm. Especially preferred is a size in a range between about 2 μm and 6 μm. The size is defined as the diameter or a maximum length of the agglomerate (depending on its shape). Thus, the deposition powder comprises nano particles with a mean particle size in the range between about 50 nm and 500 nm, preferably about 200 nm, which form agglomerates in the above named magnitudes.

Preferably, the calcium/phosphate molar ratio in the preferred phosphate powders is in the range between about 0.5 and 4, especially preferred in a range between 1 and 2.5, and even more preferred in a range between about 1.5 and 1.8.

Preferably, the powder mixture is characterized in that the deposition powder has hydroxylapatite, tricalcium phosphate and/or octocalcium phosphate. In other words, the already discussed phosphate powder is hydroxylapatite, tricalcium phosphate and/or octocalcium phosphate. Preferably, the hydroxylapatite, tricalcium phosphate and/or octocalcium phosphate is calcinated at about 1200° C. Naturally it is preferable that the hydroxylapatite, tricalcium phosphate and/or octocalcium phosphate is in the form of the above named agglomerates of nano particles.

Expediently, the powder mixture is characterized in that the deposition powder and/or the carrier powder is the carrier of medication and/or other additives. Preferably, an additive can for example be a colouring agent with which the colour of the remineralization film applied or to be applied can be adjusted to the colour of the existing teeth. Naturally, the colour of the teeth can also be altered if desired, for example whitened. The additives may include substances which promote or support the remineralization of teeth and protect the teeth against other influences. Preferably, the powder mixture can be provided with different taste varieties via at least one additive. Advantageously, an additive can, for example, also be a colour marker which shows the operator which regions of the teeth have already been treated. Expediently, the colour marker is designed such that it loses its colour after a determinable time, in other words that it becomes invisible again to prevent the treated regions of the teeth becoming unnaturally coloured.

According to the invention, a powder jet device, particularly for use in dentistry, comprises a mixing unit and a control unit, whereby the mixing unit is designed to produce a fluid/powder mixture from a fluid stream and/or an air stream and at least one powder, characterized in that the powder jet device has a deposition function by which the powder jet device can form a remineralization film on tooth surfaces and that the formation of the remineralization can be influenced by the control unit. Advantageously, the powder is the powder mixture according to the invention.

Expediently, the mixing unit is designed to mix the powder mixture, the fluid stream, particularly a water stream, and/or an air stream. Also preferably, the mixing unit can be designed to mix the powder mixture according to the invention, preferable consisting of a deposition powder and a carrier powder. Also preferably, the deposition powder can first be mixed with water or air and then with the carrier powder or vice versa. In principle, the difficulty is that the deposition powder is very fine and difficult to swirl. It is therefore technically easier to use an already mixed powder mixture according to the invention. Expediently, the powder jet device comprises a manual device with a connection to the fluid/powder mixture. Preferably, the powder jet device also comprises a stationary unit whereby the stationary unit comprises a powder container to hold the powder mixture according to the invention and is connected with the manual device via supply lines for air, water, powder mixture, etc. Advantageously, the powder container is designed to form the mixing unit. Also preferably, the powder jet device can be designed as a manual device which contains the powder container and the mixing unit and is connected, for example via supply lines for air and water, with a stationary unit. In this case, the fluid/powder mixture is only formed in the manual device.

Advantageously, the powder jet device is characterized in that the control unit influences the formation of the remineralization film via the ratio of the fluid stream related to the portion of the powder or powder mixture. Expediently, the powder is the powder mixture according to the invention, which contains a carrier powder. The less the control unit regulates the water portion, the higher is the deposition function. If the carrier powder is a cleaning powder, the control unit can increase the cleaning function by increasing the proportion of water, Advantageously, the switch can be automatic and is then indicated to the operator of the powder jet device. Naturally, it is possible to switch deliberately between cleaning function and deposition function (either only cleaning or only applying a remineralization film). But both functions can also be used simultaneously, whereby preferably, for example, the portion of the cleaning function in relation to the deposition function can be regulated via the fluid portion. As already indicated, it is advantageous to perform the cleaning first and then to apply the remineralization film. The time necessary for each is preferably calculated automatically by the control unit, which expediently is parametrizable in a suitable manner, for example by entering the size of the region or the number of teeth to be treated. The operator is then conveniently told when the cleaning can be ended or when the application of the remineralization film can begin, and for how long the regions must be treated to achieve a remineralization film of sufficient thickness.

Advantageously, the control unit can also automatically switch from the cleaning function to the deposition function. Expediently, the operator can also directly adjust the water portion via a control means such as a rotary switch, an electronic control panel or an appropriately parametrized touch screen. Naturally, the above named characteristics and advantages can analogously apply to increasing or decreasing the water pressure which is naturally correlated with the amount of water. The same applies to air pressure which also influences the composition of the fluid/powder mixture. Advantageously, the control unit is also provided with an interval function which has the effect that the fluid/powder mixture is ejected at certain determinable intervals to form the remineralization film. Preferably, this is used to form a remineralization film of very even thickness. Thus, the interval can be expediently adjusted such that ejection continues until a remineralization film of desired layer thickness is achieved. During that time, the operator preferably holds the nozzle of the powder jet device in the same place of the tooth surface. When the interval has ended, the operator knows that the nozzle must now be slightly moved. In that fashion, the operator can treat a whole tooth or the tooth surfaces step by step, thus achieving a layer of even thickness.

Preferable, the powder jet device is characterized in that the control unit influences the formation of the remineralization film via pressure, temperature and/or application speed of the fluid/powder mixture. While being diffused into the air, the fluid/powder mixture possesses kinetic energy which is converted into heat when it hits the tooth surface. This heat is preferably utilized to form the remineralization film. In the nano second range, temperatures of about 500 to 600° C. can occur. Advantageously, this causes the nano particles or the agglomerates of the powder mixture to fuse together. Also advantageously, the heat causes the particles or components to be deposited to the already existing remineralization film and to the tooth surface(s).

Naturally, an increase in pressure (of the air stream as well as the water stream) can change the kinetic energy of the fluid/powder mixture, which means that the formation of the remineralization film can be influenced. This also applies to the increase or decrease in the temperature or speed of the fluid/powder mixture.

Expediently, the powder jet device is characterized in that the powder jet device has a cleaning function, whereby the fluid stream for the cleaning function is preferably >20 ml/min, and the fluid stream for the deposition function is preferable about 2 to 10 ml/mm.

Also preferably, the powder jet device is characterized in that it can be switched between the deposition function and the cleaning function. It is advantageous when two defined amounts of water or water portions are provided, between which the device can be switched. When switching between cleaning function and deposition function, it is also possible in addition or alternatively to regulate the amount of powder and/or the pressure of the device. Higher air pressure promotes the cleaning effect.

According to a preferred embodiment of the invention, the device is exclusively switched between the two operating states (cleaning/deposition) by reducing or increasing the amount of liquid or fluid. Preferably, the powder jet device can be designed such that the two operating states can be pre-set and that the operator only switches between the two operating states during treatment, depending on which function is required.

Thus, advantageously, the powder jet device is characterized in that the powder jet device has one predeterminable operating state for deposition and that the powder jet device has one predeterminable operating state for cleaning, and that the powder jet device can be switched back and forth between these two predetermined operating states.

Also advantageously, the powder jet device is characterized in that the powder jet device is provided with a heating arrangement for preheating the powder. Preferably, this can be used to influence the formation of the remineralization film. The above mentioned effects (concerning the influence of temperatures) were already described. Naturally, the fluid stream can also be preheated.

Expediently, the powder jet device is also equipped with a light source which provides a light ray that illuminates the tooth region being treated at the moment. Thus, the operator knows in which region the remineralization film is being applied or which region is being cleaned. This allows for a remineralization film layer of particularly even thickness.

The invention also relates to a suitable means for remineralizing tooth surfaces. This means is produced by using the powder mixture according to the invention plus optionally other components as for example finely grained substances such as silica gel, bleaches, analgetics, bactericides or flavourings added to the means. Air and water can also be added to the means to enable it to be applied to the tooth surfaces treated with the powder jet device.

According to the invention, a method of remineralizing teeth comprises the steps of:
 providing a powder or powder mixture;
 providing a fluid stream and/or air stream;
 mixing the fluid stream and/or air stream with the powder or powder mixture to form a fluid/powder mixture;
 depositing the fluid/powder mixture onto the teeth;
 controlling the deposition by adjusting a ratio between the fluid stream and the powder or powder mixture.
Preferably, the method also comprises the step of:
 cleaning the teeth.

According to the invention, the powder mixture is preferably used together with a fluid, preferably water, in a medical device, in particular a dental powder jet device, to clean and remineralize teeth, whereby it is possible to switch between the cleaning function and the deposition function of the powder mixture via the amount of fluid with which the powder mixture can be mixed.

Naturally, the above named advantages and characteristics of the powder mixture according to the invention also apply to the powder jet device according to the invention, the method according to the invention and the use according to the invention as well as to any combination thereof.

The invention claimed is:

1. A powder mixture, in particular for the remineralization of teeth, characterized in that the powder mixture comprises a deposition powder designed to adhere to tooth surfaces, the deposition powder comprises a plurality of agglomerates of nanoparticles,
- wherein the plurality of agglomerate nanoparticles has a specific surface area of approximately >50 m2/g,
- wherein the plurality of agglomerate nanoparticles' size is in the range between approximately 1 μm and 10 μm;
- wherein the powder mixture comprises a carrier powder adhered to the deposition powder;
- wherein the carrier powder transports the deposition powder; and
- wherein the carrier powder comprises a cleaning powder comprising one or more of sodium carbonate, glycine and alditoles.

2. The powder mixture according to claim 1, characterized in that the cleaning powder has a mean particle size ranging between 10 μm and 100 μm.

3. The powder mixture according to claim 1 characterized in that the powder mixture offers a cleaning function and a deposition function, whereby the deposition function serves to remineralize the teeth.

4. The powder mixture according to claim 1, characterized in that the deposition powder is a phosphate powder, and that the portion of the phosphate powder in the powder mixture is preferably between about 0.5% and 30%.

5. The powder mixture according to claim 4, wherein the deposition further comprising calcium carbonate, one of the preceding claims, characterized in that the calcium/phosphate molar ratio of the deposition powder is in the range between approximately 0.5 and 4.

6. The powder mixture according to claim 1, one of the preceding claims, characterized in that the deposition powder comprises hydroxylapatite, tricalcium phosphate and/or octocalcium phosphate.

7. The powder mixture according to claim 1, one of the preceding claims, characterized in that the deposition powder and/or the carrier powder is a carrier of medication and/or other additives.

8. Use of a powder mixture according to one of claims 1, 2-4, and 5-7, if applicable, together with other finely grained substances such as silica gel, bleaches, analgetics, bactericides and/or flavourings, to produce a means for remineralizing teeth.

9. A method for the remineralization of teeth, comprising the steps of:
- providing a powder or powder mixture according to one of claims 1, 2-4, and 5-7;
- providing a fluid stream and/or air stream;
- mixing the fluid stream and/or air stream with the powder or powder mixture to form a fluid/powder mixture;
- depositing the fluid/powder mixture onto the teeth;
- controlling the deposition by adjusting a ratio between the fluid stream and the powder or powder mixture.

* * * * *

UNITED STATES PATENT AND TRADEMARK OFFICE
CERTIFICATE OF CORRECTION

PATENT NO. : 10,596,076 B2  
APPLICATION NO. : 15/022539  
DATED : March 24, 2020  
INVENTOR(S) : Marcel Donnet Page 1 of 1

It is certified that error appears in the above-identified patent and that said Letters Patent is hereby corrected as shown below:

On the Title Page

Under abstract "9 Claims, No Drawing Sheets" should read --7 Claims, No Drawing Sheet--.

In the Claims

Column 8, Line 16, cancel the text beginning with "8. Use of a powder mixture" to and ending "fluid stream and the powder or powder mixture." in Column 8, Line 30.

Signed and Sealed this  
Seventh Day of July, 2020

Andrei Iancu  
*Director of the United States Patent and Trademark Office*